United States Patent [19]
Kobayashi

[11] Patent Number: 5,577,095
[45] Date of Patent: Nov. 19, 1996

[54] MEDICAL EXAMINATION APPARATUS

[75] Inventor: Shigeo Kobayashi, Chiba, Japan

[73] Assignee: Sony Corporation, Tokyo, Japan

[21] Appl. No.: 340,858

[22] Filed: Nov. 15, 1994

[30] Foreign Application Priority Data

Nov. 25, 1993 [JP] Japan .................. 5-319023

[51] Int. Cl.$^6$ .................................................. A61B 6/08
[52] U.S. Cl. ........................................... 378/206; 378/205
[58] Field of Search ............................. 378/20, 205, 206

[56] References Cited

U.S. PATENT DOCUMENTS

4,502,147  2/1985  Michaels .......................... 378/206
4,538,289  8/1985  Scheibengraber .................. 378/206
5,188,110  2/1993  Sugimoto .......................... 378/206

*Primary Examiner*—Don Wong
*Attorney, Agent, or Firm*—Ronald P. Kananen

[57] ABSTRACT

An examination apparatus is equipped with a medical examination unit for performing medical examination of an examination body, and a medical examination area display means for indicating, with light, a medical examination area on the examination body placed in the medical examination unit.

9 Claims, 10 Drawing Sheets

MEDICAL EXAMINATION APPARATUS

BACKGROUND OF THE INVENTION

The present invention relates to a medical examination apparatuses such as an X-ray CT apparatus.

When an operator takes an X-ray CT images of a patient using a conventional X-ray CT apparatus, he performs positioning of the patient according to the following steps.

(1) The patient places himself on a patient table. (In some cases, several operators move the patient from his bed to the patient table.)

(2) The operator places the patient into a scanner gantry by moving the patient table vertically and horizontally by manual operations. (Coarse patient positioning operation)

(3) A light source of a localizer (projector for the patient positioning) is turned on in response to the operator's operations on the patient table.

(4) Looking at a portion on the surface of the patient marked by light from the localizer, the operator determines (finely adjusts) an X-ray irradiating position.

(5) A scanogram image (X-ray CT image) is taken by X-ray irradiation.

(6) The scanogram image is displayed on an image monitor of an operation console. The operator determines, on the image monitor, an X-ray CT image taking position by using a track ball, for instance. At the same time, he determines X-ray CT image taking conditions and image reconstruction conditions. The image reconstruction conditions consist of a plurality of parameters such as the number of display matrices, a filter shape, a magnification factor and a reconstruction computing area.

(7) An X-ray CT image is taken, and an image analysis is performed thereon.

The conventional X-ray CT apparatus, in which the patient positioning is performed according to the above steps, has no interface between the light of the localizer and the image reconstruction conditions.

The localizer of the conventional X-ray CT apparatus will be described with reference to FIGS. 7 and 8.

Figure 7:
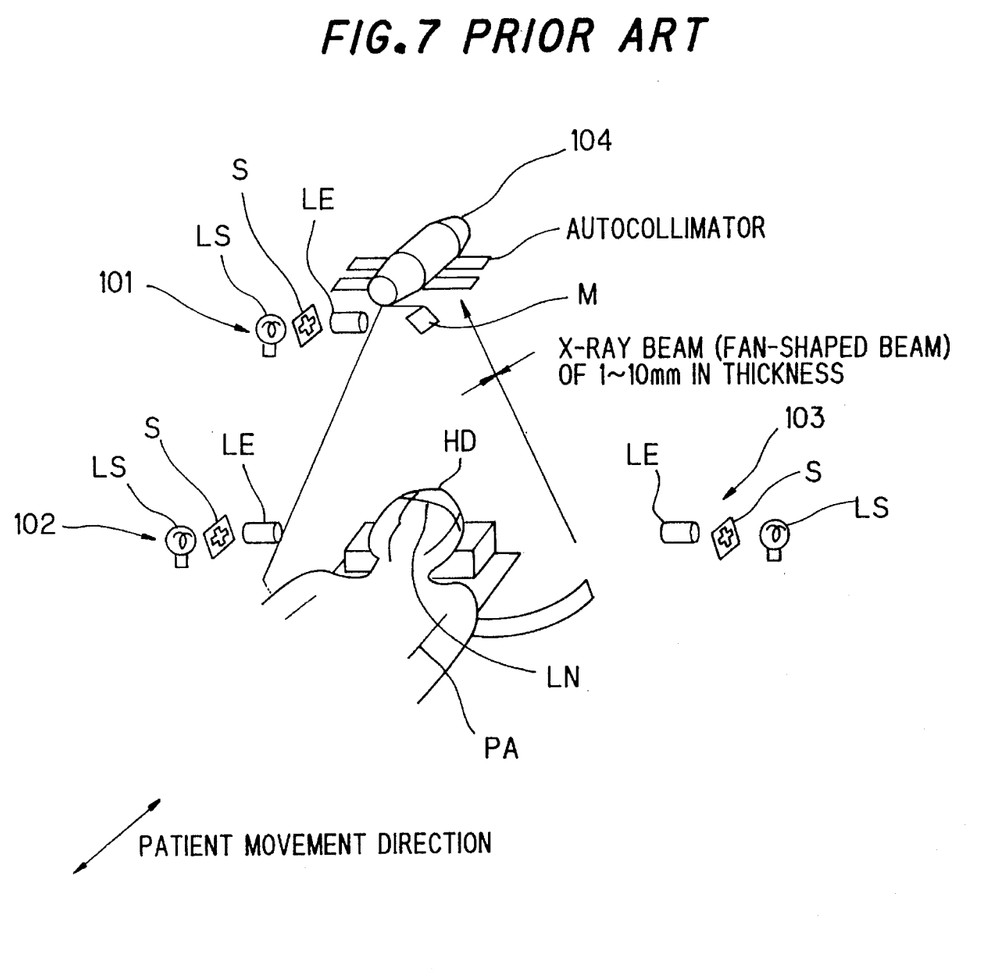
FIG. 7 shows a configuration of a conventional X-ray CT apparatus.

As shown in FIG. 7, the X-ray CT apparatus has a top localizer 101, a left-side localizer 102 and a right-side localizer 103. Each of the localizers 101–103 is composed of a light source L, a slit S and a lens LE (and a mirror M).

It is a commonly employed scheme that the localizers 101–103 are linked with (i.e., turned on together with) a switch of the scanner gantry or patient table.

Figure 8:
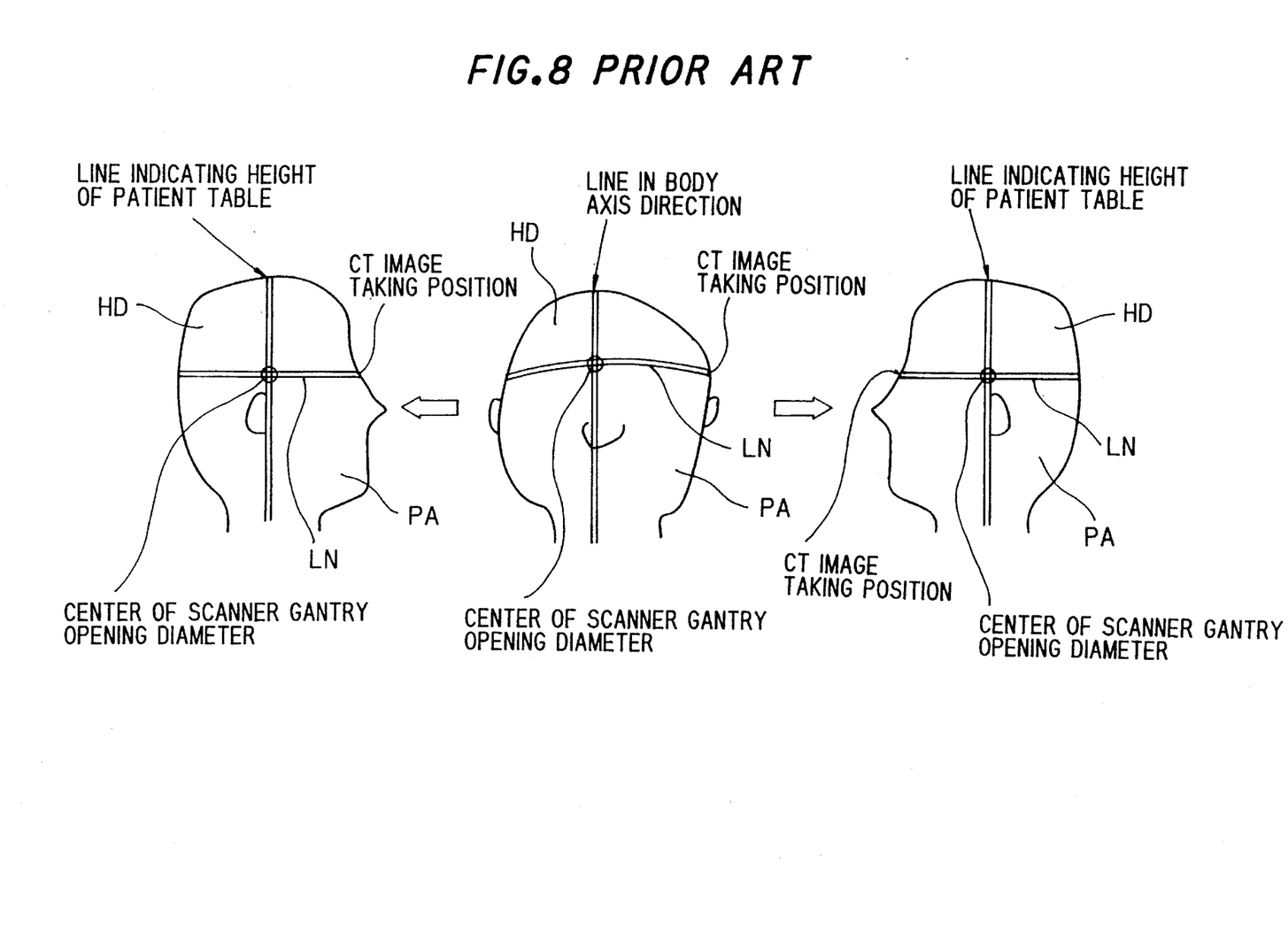
FIG. 8 shows an example of a scheme of forming lines of light on the head of a patient in the conventional X-ray CT apparatus of FIG. 7.

In the X-ray CT apparatus of FIG. 7, lines LN of light as a mark on the body surface of a patient PA is drawn as shown in FIG. 8 in accordance with, for instance, a cruciform aperture of the slit S. FIG. 8 shows a head HD of the patient PA, on which plural sets of cruciform lines LN of light are drawn.

Optics of each of the localizers 101–103 for generating the lines LN is fixed to the scanner gantry, and the width of tile cruciform aperture of the slit S is fixed. Therefore, it is impossible to change the with of the lines LN, nor move the lines LN of light themselves.

Figure 9:
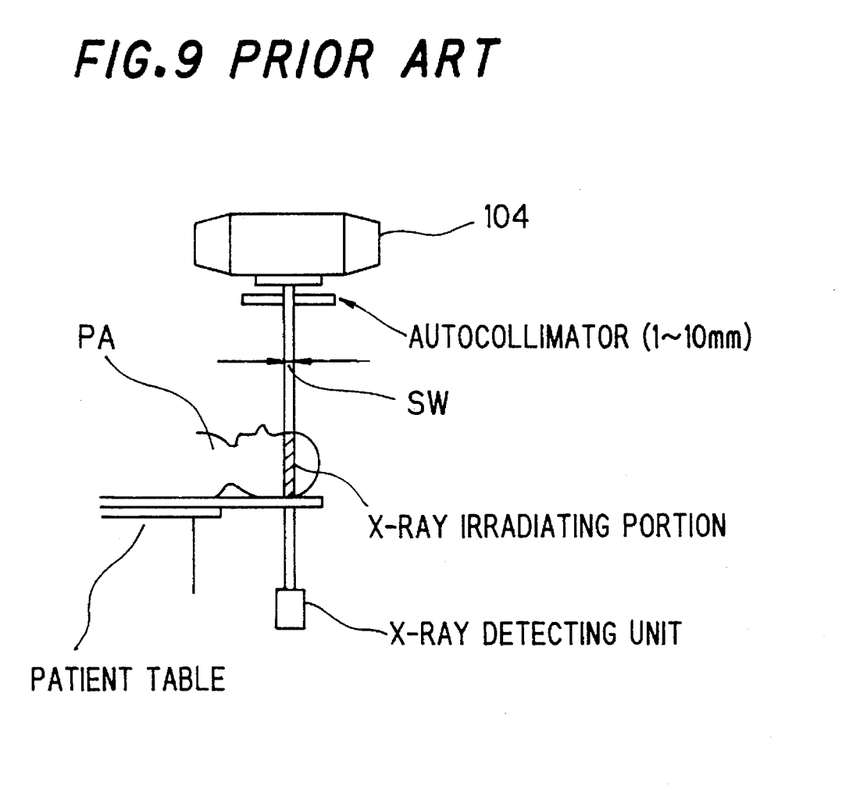
FIG. 9 shows an example of X-ray irradiation in the conventional X-ray CT apparatus of FIG. 7.

As shown in FIG. 9, in the conventional X-ray CT apparatus, the irradiation width (called "slice thickness" SW) of X-rays emitted from an X-ray tube 104 is varied with a part to be taken with X-rays. For example, the irradiation width is 10 mm when an abdomen is to be imaged; and is 5 or 2 mm for a head. Therefore, the lines LN of light of the conventional localizer basically serves to indicate only the center of the X-ray irradiation width.

With the above-described construction, the conventional X-ray CT apparatus has the following problems.

(1) It is hard for an operator to visually recognize the irradiation width (slice thickness SW) of X-rays emitted from the X-ray tube 104 from a marker (lines LN of light) of the localizer.

This problem results from the fact that the width of the lines LN of light cannot be changed because the optics of FIG. 7 are fixed to the scanner gantry and the cruciform aperture of the slit S is fixed.

Figure 10:
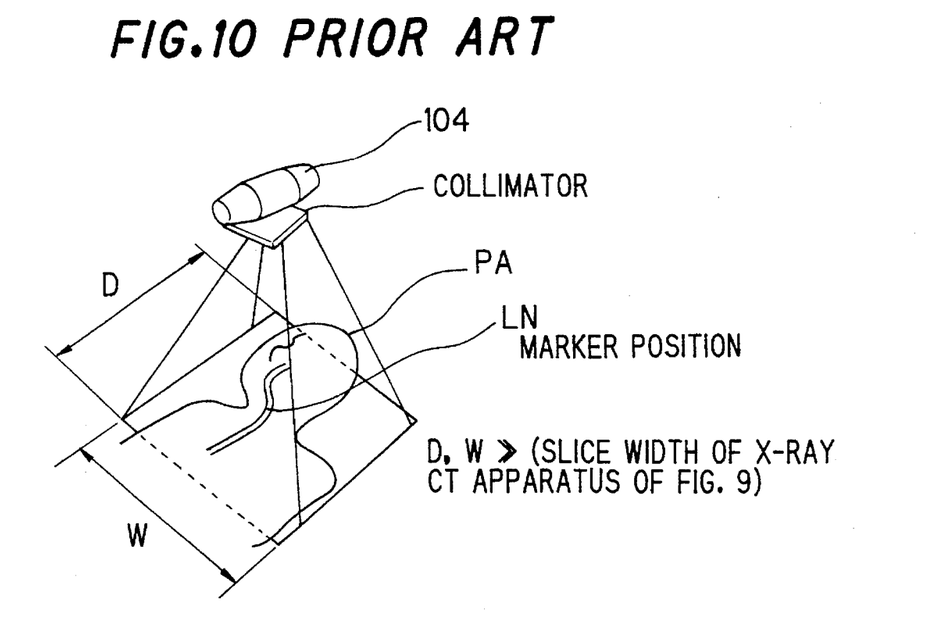
FIG. 10 is a perspective view showing an example of X-ray irradiation in another conventional X-ray Ct apparatus.

(2) In the case of an X-ray CT apparatus capable of obtaining data in a "surface" (see FIG. 10) in contrast to the conventional X-ray apparatus of FIG. 9 in which an irradiation portion of X-rays emitted from the C-ray tube 104 has a "line" shape, the marker (lines LN of light) of the conventional localizer would be improper.

That is, the marker (lines LN of light) of the localizer cannot cover the X-ray irradiation width. This problem results from the facts that in the apparatus of FIG. 10 the values of the width W and the length D of a surface for data acquisition are much larger than the slice width SW of the conventional X-ray CT apparatus of FIG. 9, and that, as described above, the optics of the localizers 101–103 are fixed to the scanner gantry.

Figure 11:
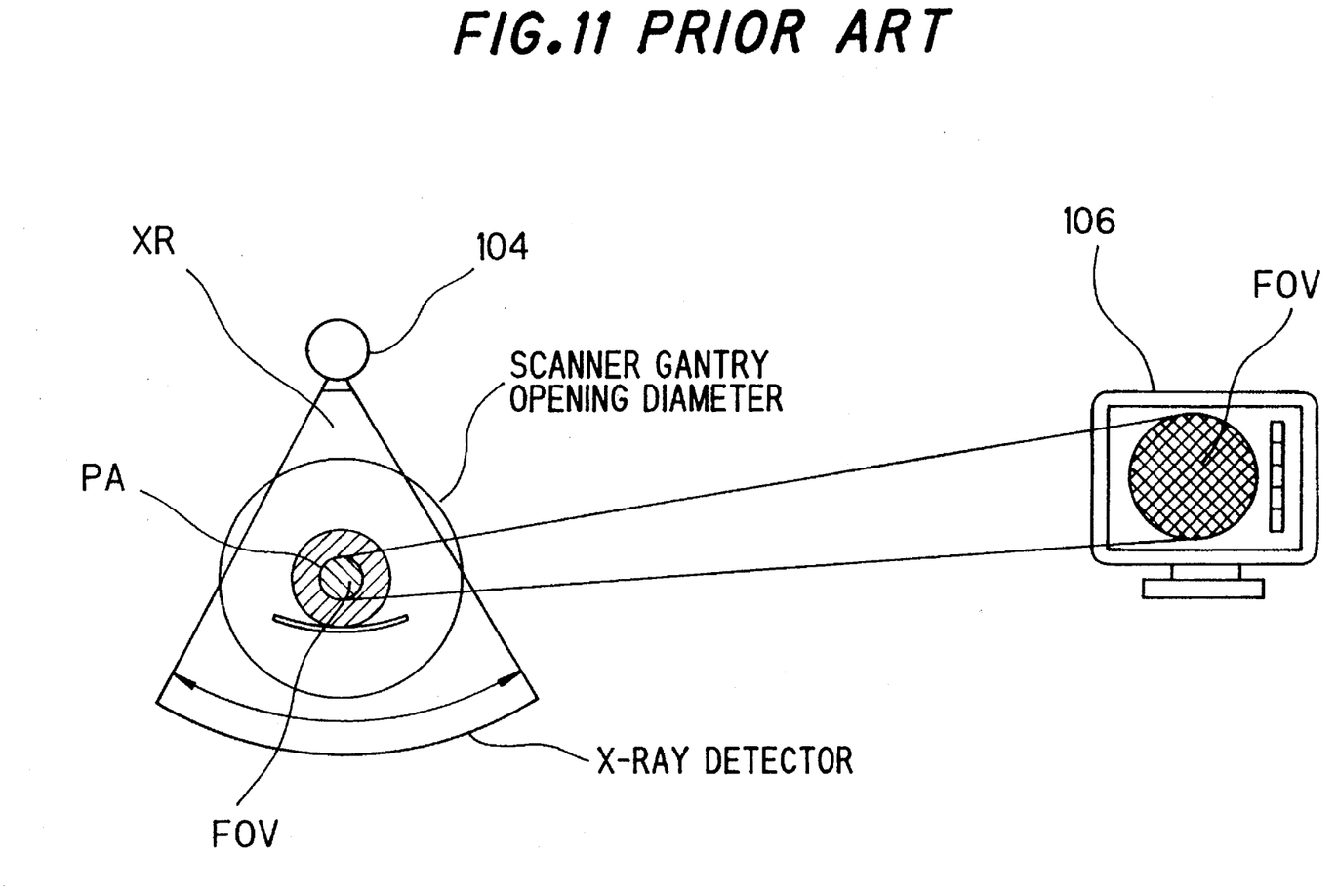
FIG. 11 shows an example of displaying an image corresponding to a reconstruction computing area in the conventional X-ray CT apparatus of FIG. 7.

Referring to FIG. 11, a description will be made of a relationship between an X-ray irradiation area XR and an image reconstruction area FOV in the conventional X-ray CT apparatus of FIG. 7.

When an examination body (patient) PA is irradiated with X-rays emitted from the X-ray tube 104, data is obtained from all the irradiated area. However, an image processing device computes using image reconstruction area (FOV: field of view) that has been set in advance through an operation console, and an image corresponding to the image reconstruction area FOV is displayed on an image monitor 106.

The measurement data is stored in a storage device immediately after completion of the X-ray irradiation. Therefore, at a later time, the operator can reconstruct again an image corresponding to the image reconstruction area FOV and display it on the image monitor 106.

The image reconstruction area FOV is a circular area having, as its center, the center of the X-ray optical system (i.e., the center of the opening of the scanner gantry).

With the above-described construction, the conventional X-ray CT apparatus has the following problems.

(1) It is hard for an operator to visually recognize the reconstruction computing area FOV from a marker (lines LN of light) of the localizer.

This is so because, as described above, in the conventional X-ray CT apparatus the lines LN of light serve only as a marker for positioning an X-ray irradiating portion with no consideration made of the reconstruction computing area FOV. Further, the conventional apparatus does not have a function of causing a marker of the localizer to move in accordance with with the reconstruction computing area FOV. Such a function is not even necessary.

(2) The fact that the reconstruction computing area FOV cannot be recognized by use of the localizer leads to an increase of a time spent by a patient at examination and a reduction of the patient throughput.

Assume that X-ray irradiation is performed once and an X-ray CT image is obtained with a reconstruction computing area set by an operator from his experience. If a resulting displayed X-ray CT image lacks a portion to be monitored, image reconstruction may be performed again with data read from the storage device.

However, in some cases, this will cause an increase of a time spent by the patient at examination and a reduction of the patient throughput. That is, a time is required for the operator to judge whether a measurement has been performed correctly in an image reconstruction area FOV preset through the operation console. This problem can be avoided if the operator can correctly recognize in advance the reconstruction computing area FOV from a marker formed on the body surface of a patient PA.

SUMMARY OF THE INVENTION

The present invention has been made to solve the above problems. Therefore, an object of the present invention is to provide a medical examination apparatus which in a medical examination such as imaging of an examination body by irradiation of X-rays, allows, by use of a marker of light, an operator to easily recognize visually and quantitatively an information area for examination such as an X-ray irradiation area or a reconstruction computing area.

According to the Invention, the above object can be attained by a medical examination apparatus comprising a medical examination unit for performing medical examination of an examination body, and medical examination area display means for indicating, with light, a medical examination area on the examination body placed in the medical examination unit.

According to the invention, preferably, the medical examination unit is used to irradiate the examination body with X-rays to obtain an X-ray image, and the medical examination area is an X-ray irradiation area.

According to the invention, preferably, the medical examination unit is used to irradiate the examination body with X-rays to obtain an X-ray image, and the medical examination area is an image reconstruction area for the examination body in which area the X-ray image is to be obtained by irradiation of the X-rays.

According to the invention, the medical examination area display means preferably comprises a light source for emitting the light, and an optical system for shaping the light emitted from the light source into a two-dimensional light illumination area on the examination body in accordance with the medical examination area.

Further, according to the invention, the optical system preferably comprises light width setting means for setting the width of the light in a first direction, and light scanning means for forming the two-dimensional light illumination area by scanning the examination body in a second direction with the light having the width that has been set in the first direction.

The light width setting means may be a slit, and the light scanning means may be a swinging mirror.

With the above constitution, when medical examination is performed on an examination body by the medical examination unit, the medical examination area display means indicates, with light, a medical examination area on the examination body placed in the medical examination unit.

For example, the medical examination unit irradiates the examination body with X-rays to obtain an X-ray image.

For example, the medical examination area is an image reconstruction area for the examination body in which area the X-ray image is to be obtained by irradiation of the X-rays.

The medical examination area display means causes the light source to emit light, and shapes the emitted light into a two-dimensional light illumination area on the examination body in accordance with the medical examination area.

Preferably, the optical system sets the width of the emitted light in the first direction with the light width setting means such as a slit, and forms the two-dimensional light illumination area by causing the light scanning means such as a swinging mirror to scan the examination body in the second direction with the light having the width that has been set in the first direction.

DESCRIPTION OF THE PREFERRED EMBODIMENT

A preferred embodiment of the present invention will be described hereinafter in detail with reference to the accompanying drawings.

Since the following embodiment is a specific one preferred in the invention, it includes various limitations that are technically preferred. However, it is noted that the scope of the invention is not limited to such specific modes unless there is a particular statement for limiting the scope of the invention.

Figure 1:
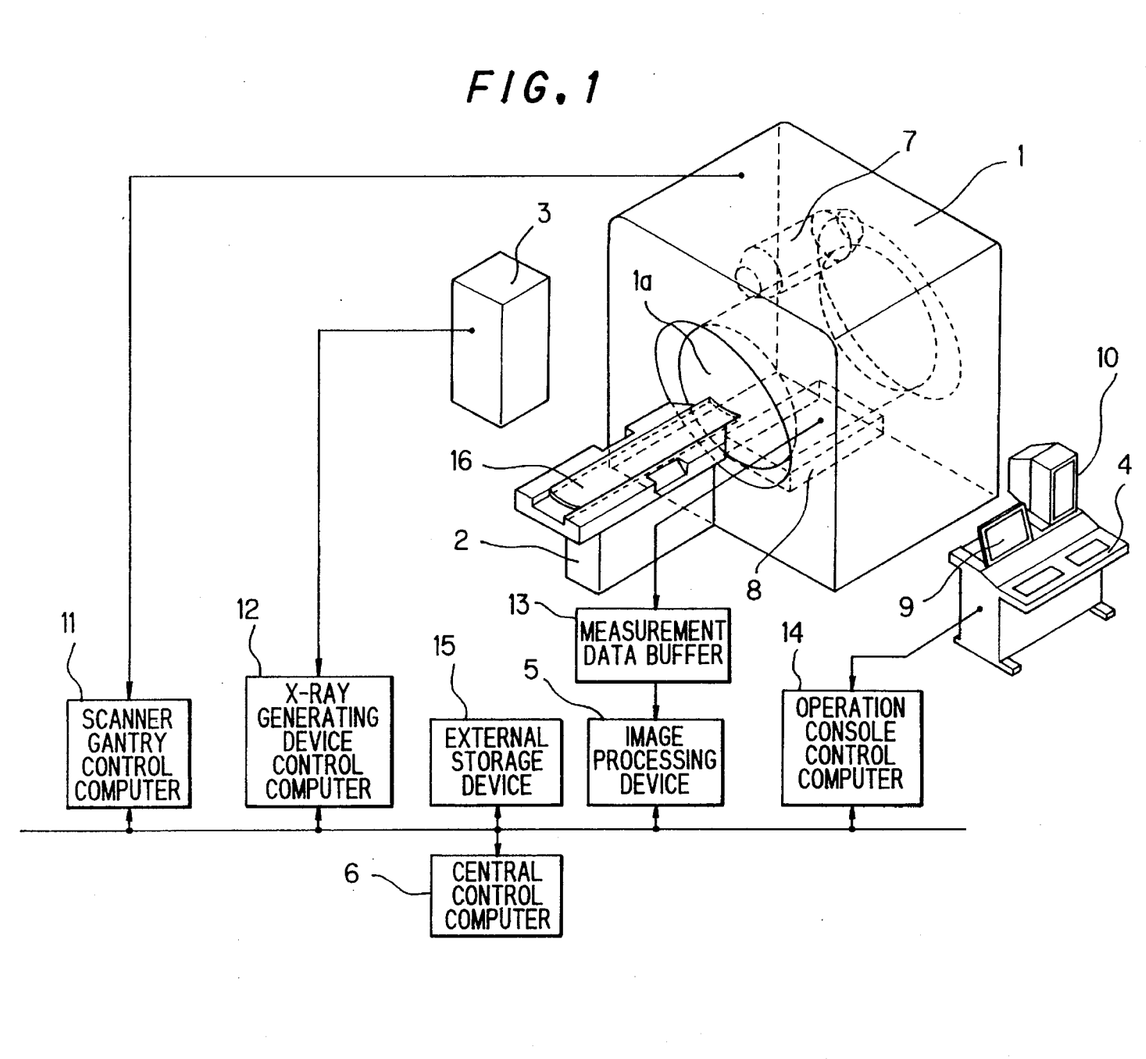
FIG. 1 shows an X-ray CT apparatus which is a preferred embodiment of a medical examination apparatus according to the present invention.

FIG. 1 shows a system configuration of an X-ray CT apparatus that is a preferred embodiment of a medical examination apparatus according to the invention.

As shown in FIG. 1, the system of the X-ray CT apparatus generally consists of various units including a scanner gantry 1, a patient table 2, an X-ray control device 3, an operation console 4, an image processing device 5, and a central control computer 6. The scanner gantry 1 is a medical examination unit.

The scanner gantry 1, X-ray control device 3 and operation console 4 have respective control computers 11, 12 and 14 for controlling those units.

The scanner gantry control computer 11 controls mechanisms in the scanner gantry 1, and also controls horizontal and vertical movements of the patient table 2. Further, the scanner gantry control computer 11 monitors inputs through an operation panel (not shown) that is provided on the surface of the scanner gantry 1, and displays positional information and height information of a top board 16 of the patient table 2.

The X-ray generating device control computer 12 controls output of generated X-rays and monitors a possible abnormality.

The operation console control computer 14 monitors inputs through switches on the operation console 4, and performs display on a 7-segment LED indicator.

In the scanner gantry 1, an X-ray tube 7 and an X-ray detector 8 are installed on tile same rotary plate (not shown) so as to be opposed to each other.

The scanner gantry 1 (medical examination unit) is a device for obtaining X-ray CT images of the examination body or body PA for medical examination.

Figure 2:
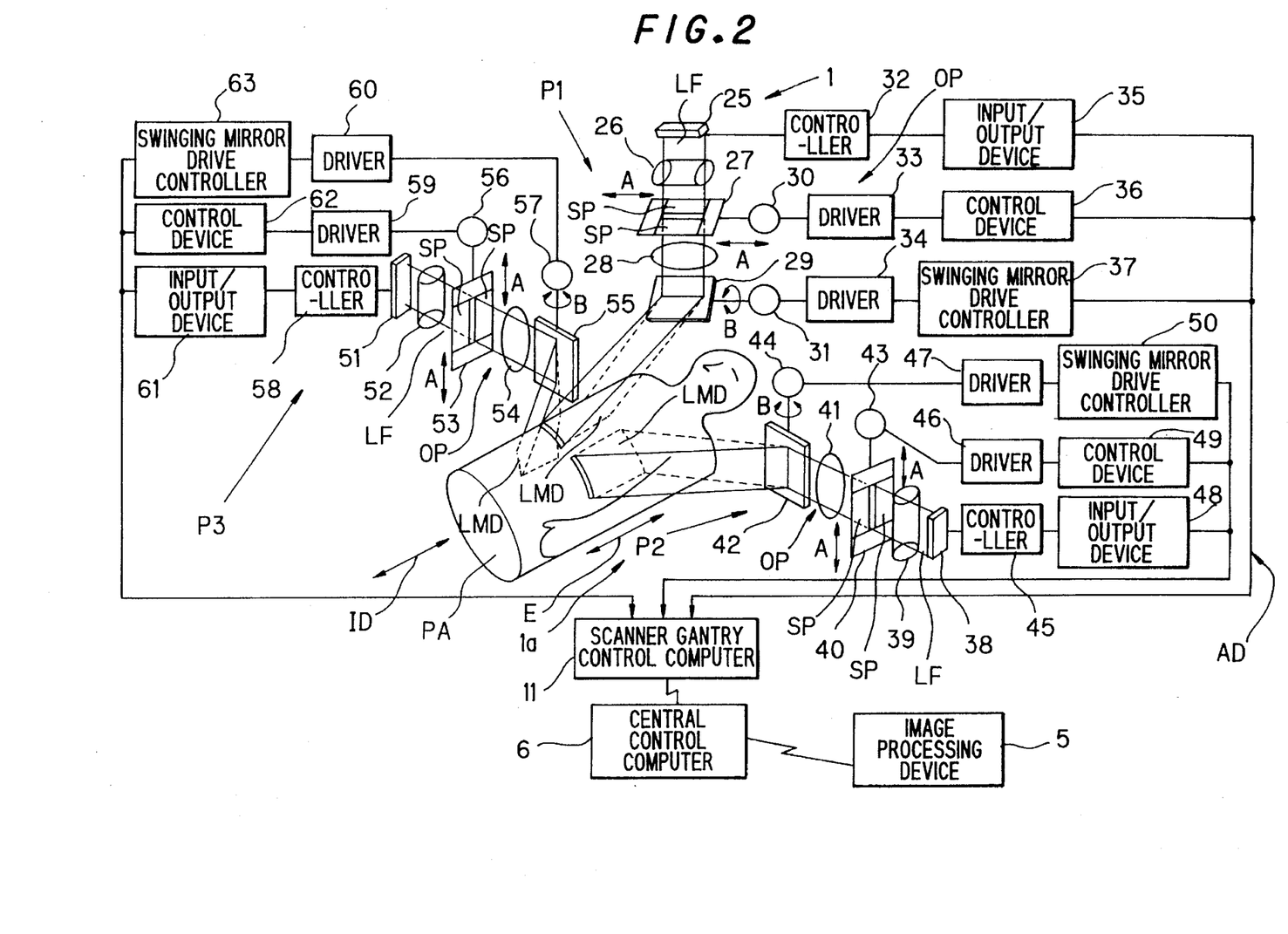
FIG. 2 shows a top localizer, a right-side localizer and a left-side localizer of the X-ray CT apparatus of FIG. 1.

Before taking X-ray CT images of the examination body (patient) PA (see FIG. 2), the operator moves the examination body PA that has been placed in advance on the top board 16 of the patient table 2 into an opening 1a of the scanner gantry 1, and positions the examination body PA by using localizers (see FIG. 2).

Data are collected by irradiating the examination body PA with X-rays while the rotary body on which the X-ray tube 7 and the X-ray detector 8 are mounted is rotated around the examination body PA. That is, X-ray CT scanning is performed on a prescribed part of the patient PA by the rotation of the rotary plate.

The data (analog signal) output from the X-ray detector 8 are converted to digital signal, and sequentially sent to a measurement data buffer 13, subjected to preprocessing such as image data compression in the image data processing device, and stored in an external storage device 15.

The data storage in the external storage device 15 is temporary. After completion of the data collection, the storage data (raw data) are sent to the image processing device 5, where an X-ray CT image is formed by a reconstructing computation. The X-ray CT image thus formed is stored into the external storage device 15.

Information for guiding or supporting a person who conducts a diagnosis or tile operator to operate the apparatus is displayed on an operation monitor 9 by the central control computer 6. Further, a system operating status is displayed on the operation monitor 9. Reference numeral 10 denotes an X-ray CT image monitor.

Now, a description will be made of a procedure for taking an X-ray CT image in the X-ray CT apparatus of FIG. 1.

Referring to FIG. 1, the person who conducts a diagnosis or the operator preliminarily moves the top board 16 on which the patient PA is placed into the opening 1a of the scanner gantry 1 (see FIG. 2). In this operation, the operator finely adjusts an X-ray irradiating portion (portion to be irradiated with X-rays) with respect to the patient PA based on lines LN of light formed on the body surface of the patient.

After completion of the positioning of the patient PA with respect to the scanner gantry 1, the operator selects and sets conditions of taking an X-ray CT image using the operation console 4 and the operation monitor 9 (see FIG. 1).

The imaging conditions depend on the imaging part of the patient PA. Particular imaging conditions corresponding to an imaging part of the patient PA are displayed, as preset information, on the operation console 4 and the operation monitor 9. The operator can alter part of the preset information.

The imaging conditions mainly consist of a plurality of parameters of X-ray generating conditions (tube voltage, tube current, scanning time, etc.) and image reconstructing conditions (the number of display matrices, filter shape, magnification factor, reconstruction computing area, etc.).

Upon determination of the imaging conditions, the central control computer 6 (see FIG. 1) reads the imaging conditions from the operation console control computer 14, changes the imaging conditions to a prescribed form, and sends messages, together with a command "prepare for imaging," to the scanner gantry control computer 11 and the X-ray generating device control computer 12.

In devices with generation of X-rays, a certain time is required from starting of a rotor (target rotary anode) of an X-ray tube until its constant speed rotation. When the rotor reaches its constant speed operation, the X-ray generating device control computer 12 (see FIG. 1) supplies a message "X-ray generating device is ready" to the central control computer 6.

While the X-ray generating device 3 (see FIG. 1) is preparing for the Imaging, the scanner gantry control computer 11 checks, upon reception of the command "prepare for imaging," whether the X-ray tube 7 and the X-ray detector 8 are located at their initial positions.

If they are not located at the initial positions (the uppermost position for the X-ray tube 7 and the lowermost position for the X-ray detector 8), the rotary plate of the scanner gantry is rotated so that they will be located at the initial positions.

When all the units have become "ready for the imaging" and the control computers 11, 12 and 14 (see FIG. 1) recognize that the corresponding units are ready, the central control computer 6 supplies a command "radiate X-rays and start to take in X-ray data" to the control computers 11, 12 and 14.

Further, the central control computer 6 supplies a command "take in X-ray data and wait for image preprocessing" to the image processing device 5.

An X-ray image is taken with the X-ray tube 7 and the X-ray detector 8 (see FIG. 1) rotating around the patient PA that is placed in the opening 1a of the scanner gantry 1. Irradiation with X-rays is performed while the X-ray tube 7 and the X-ray detector 8 are rotated by 360°. The X-ray tube 7 and the X-ray detector 8 rotate more than 360° in total (including rotations during acceleration and deceleration).

There are two X-ray generation schemes: pulsed generation scheme and continuous generation scheme. In the former scheme, 1-view (projection) data is obtained by one pulse. In the latter scheme, 1-view data is obtained by one sampling. As the number of views increases, the information quantity increases to improve the image quality. On the other hand, the image processing device is required to be able to process a large amount of data at high speed.

Since the data output from the X-ray detector 8 (see FIG. 1) is an analog signal, it is subjected to analog-to-digital conversion when it is transferred to the measurement data buffer 13.

The thus-produced data In the form of a digital signal is subjected to image preprocessing such as data compression in the image processing device 5, and stored into the external storage device 15.

When the X-ray irradiation has been completed and all the data have been transferred to the measurement data buffer 13, the image processing device 5 (see FIG. 1), upon reception of a command "perform image reconstruction computing" from the central control computer 6, forms an X-ray CT image based on the above-described image reconstructing conditions. The X-ray CT image thus formed is displayed on the image monitor 10, and stored into the external storage device 15 together with the raw data in some cases.

If messages, which are sent from the central control computer 6 in advance of each X-ray image taking, include a feed amount per each measurement of the top board 16 of the patient table 2, the scanner gantry control computer 11 have the top board 16 move horizontally after completion of each measurement.

Now, reference is made to FIG. 2.

FIG. 2 shows the patient PA placed on the patient table 2 and an internal configuration of the scanner gantry 1.

The examination body (patient) PA is placed on the top board 16 of the patient table 2 (see FIG. 1). The scanner gantry control computer 11 and the central control computer 6 are connected to each other through a communication line. The image processing unit 5 and the central control computer 6 are also connected to each other through a communication line.

The scanner gantry 1 has, in its inside, an area display means AD for medical examination (see FIG. 2), which is equipped with three localizers (patient positioning devices) P1–P3.

Symbol P1 denotes a top localizer having a top projector and a control unit therefor. P2 denotes a right-side (as viewed from the patient inserting direction) localizer having a right-side projector and a control unit therefor. P3 denotes a left-side localizer having a left-side projector and a control unit therefor.

The projectors and the control units of the localizers P1–P3 are of the same type, and can be controlled independently of each other.

Reference numerals 25, 38 and 51 represent the projectors, i.e., light sources of the respective localizers P1–P3. Controllers 32, 45 and 58 control the illuminance and turning on/off of the light sources 25, 38 and 51, respectively.

The controllers 32, 45 and 58 of the light sources are respectively connected to input/output devices 35, 48 and 61 that are directly connected to the scanner gantry control computer 11.

With the above configuration, the scanner gantry control computer 11 can control the illuminance of light emitted from each of the light sources 25, 38 and 51 and the turning on/off of those light sources. The light sources 25, 38 and 51 may be a LED lamp, an incandescent lamp, etc. which are harmless to a patient.

Each of the localizers P1–P3 has optics OP for shaping the light emitted from the light source 25, 38 or 51 into a two-dimensional or curved-surface light illumination area on the examination body PA in accordance with an area for medical examination. The area for medical examination means the X-ray irradiation area XRA or the image reconstruction area FOV shown in FIG. 3.

Figure 3:
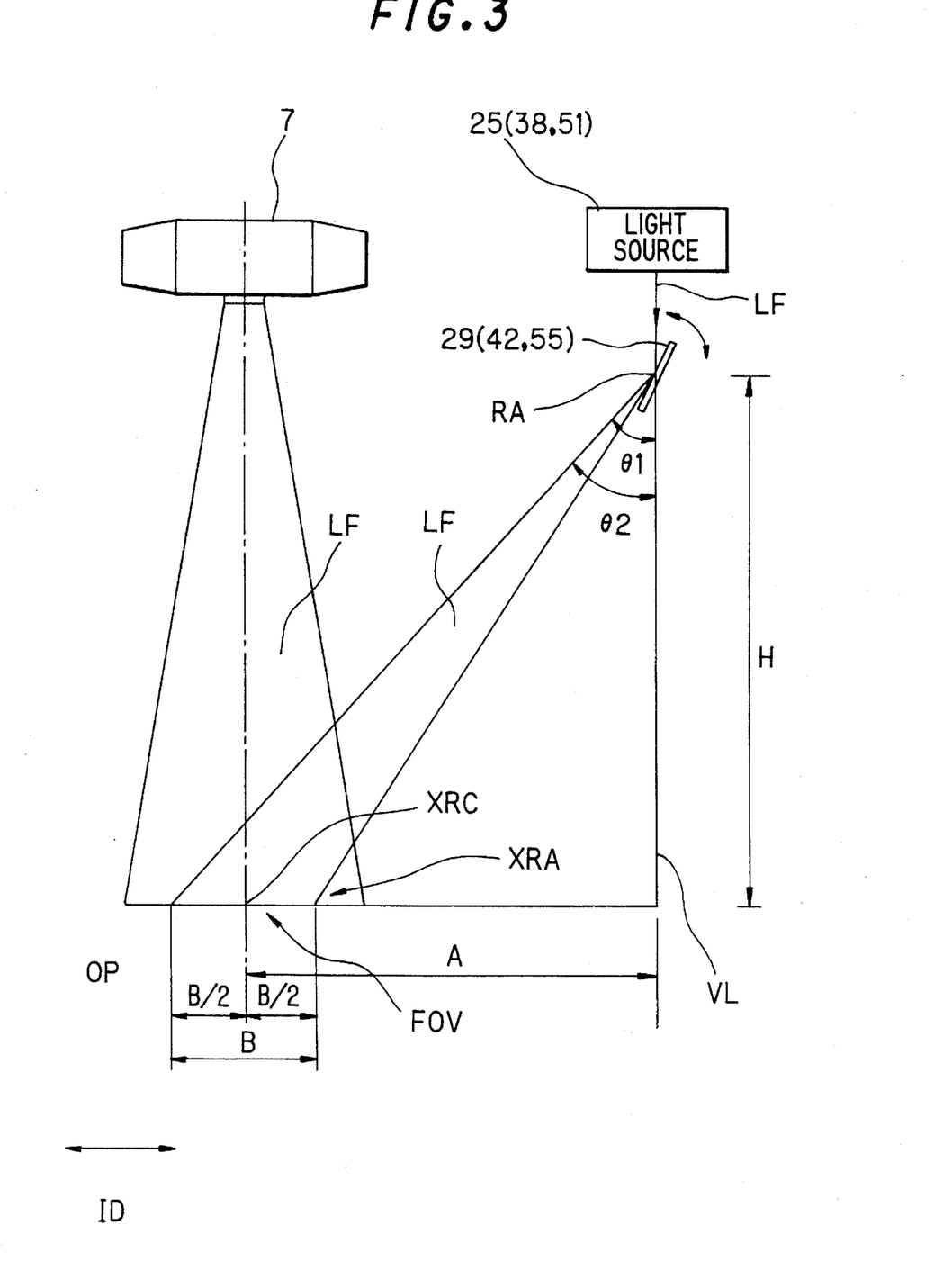
FIG. 3 shows in detail optics of the top localizer (representing optics of the three localizers) of the X-ray CT apparatus of FIG. 1.

By shaping the light emitted from the light source 25, 38 or 51 into the light illumination area on the examination body PA in accordance with the X-ray irradiation area XRA or the image reconstruction area FOV, the person who conducts a diagnosis or the operator can recognize the X-ray irradiation area XRA or the image reconstruction area FOV visually and quantitatively.

The optics OP will be described with reference to FIG. 2.

Each optic arrangement has a converging lens, a slit mechanism, a collimator lens and a swinging mirror.

In each of the localizers P1–P3, a cylindrical converging lens 26, 39 or 52 applies converging action to the light emitted from the light source 25, 38 or 51, i.e., converts a divergent light beam into a parallel light beam.

In each of the localizers P1–P3, a slit mechanism 27, 40 or 53 has an aperture whose length can be adjusted or changed by driving. More specifically, in the slit mechanism 27, 40 or 53, shield plates SP move in the direction (first direction) indicated by arrows A in FIG. 2 being driven by a driving device 30, 43 or 56 to change the width of a light beam LF. Reference numerals 33, 46 and 59 denote drivers for the driving devices 30, 42 and 56 of the slit mechanisms 27, 40 and 53, respectively. Further, reference numerals 36, 49 and 62 denote control devices for controlling the drivers 33, 46 and 59 for the slit mechanisms 27, 40 and 53, respectively.

With the above configuration, based on a command sent from the scanner gantry control computer 11, the driving devices 30, 43 and 56 can set the slit widths at arbitrary values by moving the shield plates SP of the slit mechanisms 27, 40 and 53 or set the slit widths at current values.

In each of the localizers P1–P3 (see FIG. 2), a collimator lens 28, 41 or 54 mainly performs alignment and focus adjustment on the light beam LF.

In each of the localizers P1–P3, a swinging mirror 29, 42 or 55 can be rotated to an arbitrary angle by a driving device 31, 44 or 57. As shown in FIG. 2, the three swinging mirrors 29, 42 and 55 operate to scan the examination body PA in the second direction indicated by arrow E with the light beams LF whose widths have been adjusted in the direction (first direction) indicated by arrows A in passing through the slit mechanisms 27, 40 and 53 are scanned. Thus, a medical examination area LMD can be formed.

As described above, the medical examination area LMD has a shape that approximately corresponds to the X-ray irradiation area XRA and the image reconstruction area FOV.

The driving devices 31, 44 and 57 are connected to respective drivers 34, 47 and 60, which receive commands indicating the number of rotations, a rotation angle, a rotation speed, etc. from the scanner gantry control computer 11 via swinging mirror drive controllers 37, 50 and 63.

The swinging mirrors 29, 42 and 55 rotate in the direction indicated by arrow B to deflect the light beam LF in the front-rear direction which is the inserting direction ID of the patient PA.

Each of the swinging mirrors 29, 42 and 55 is a plane mirror, for instance. In a galvano mirror, the plane is simply rotated. A polygon mirror may also be used which has mirror-polished faces combined to assume a polygon. The invention imposes no specific limitations on the kind of the swinging mirrors 29, 42 and 55.

The light sources 25, 38 and 51 may be either CW light sources or pulsed light sources.

Referring to FIG. 3, a description will be made of how to calculate swing angles θ (θ1, θ2) of the swinging mirrors 29, 42 and 55 and the image reconstruction computing area (also called the image reconstruction area FOV).

FIG. 3 shows optics of the top localizer P1, which represents optics of the three localizers P1–P3. The optics of the right-side localizer P2 and the left-side localizer P3 have configurations similar to the configuration of FIG. 3.

In FIG. 3, reference symbol H denotes a height of a rotation axis RA of the swinging mirror as measured from a central axis OP of the scanner gantry opening. The rotation axis RA is located at the position where the light beam LF is reflected by the swinging mirror 29 (42, 55).

In FIG. 3, reference symbol A denotes a distance from the center XRC of the X-ray irradiation area XRA to the rotation axis RA of the swinging mirror 29 (42, 55). Symbol B denotes a depth (when the scanner gantry main body 1 is seen from the front side) of the image reconstruction area FOV.

The swing angles θ of the swinging mirror 29 (42, 55) are set at θ1 and θ2 that are measured from a vertical line VL passing through the rotation axis RA. As shown in FIG. 3, θ1 and θ2 correspond to both end positions of the depth B of the image reconstruction area FOV. The swing angles θ1 and θ2 are represented by Equations (1) and (2), which have simple forms (when the light beam LF is parallel with the vertical line VL).

$$\theta_1 = \tan^{-1}(A-B/2)/H \quad (1)$$

$$\theta_2 = \tan^{-1}(A+B/2)/H \quad (2)$$

In the right-side optics of the right-side localizer P2 and the left-side optics of the left-side localizer P3, the swing angles θ1 and θ2 of the swinging mirror 42 or 55 are calculated by substituting the distance from the central axis OP of the opening to the rotation axis RA of the swinging mirror into the height H of Equations (1) and (2).

The above description has been made with an assumption that the swing angles θ1 and θ2 of the swinging mirror 29 (42, 55) are calculated so that the light emitted from the light source (projector) 25 (38, 51) represents the image reconstruction area FOV on the central axis OP of the scanner gantry opening 1a.

Figure 4:
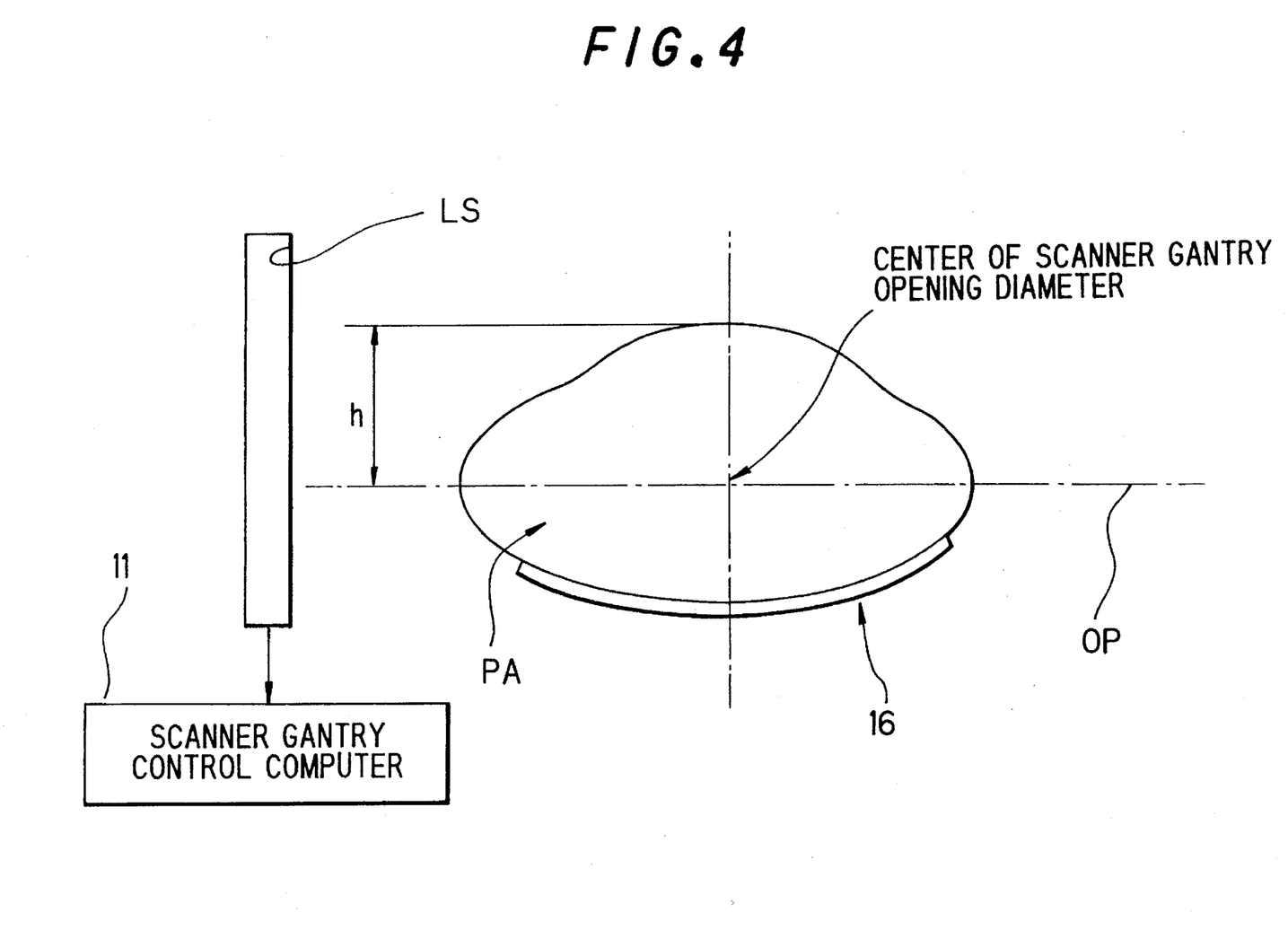
FIG. 4 shows a case In which the abdomen of a patient is irradiated with X-rays in the X-ray CT apparatus of FIG. 1.
Figure 5:
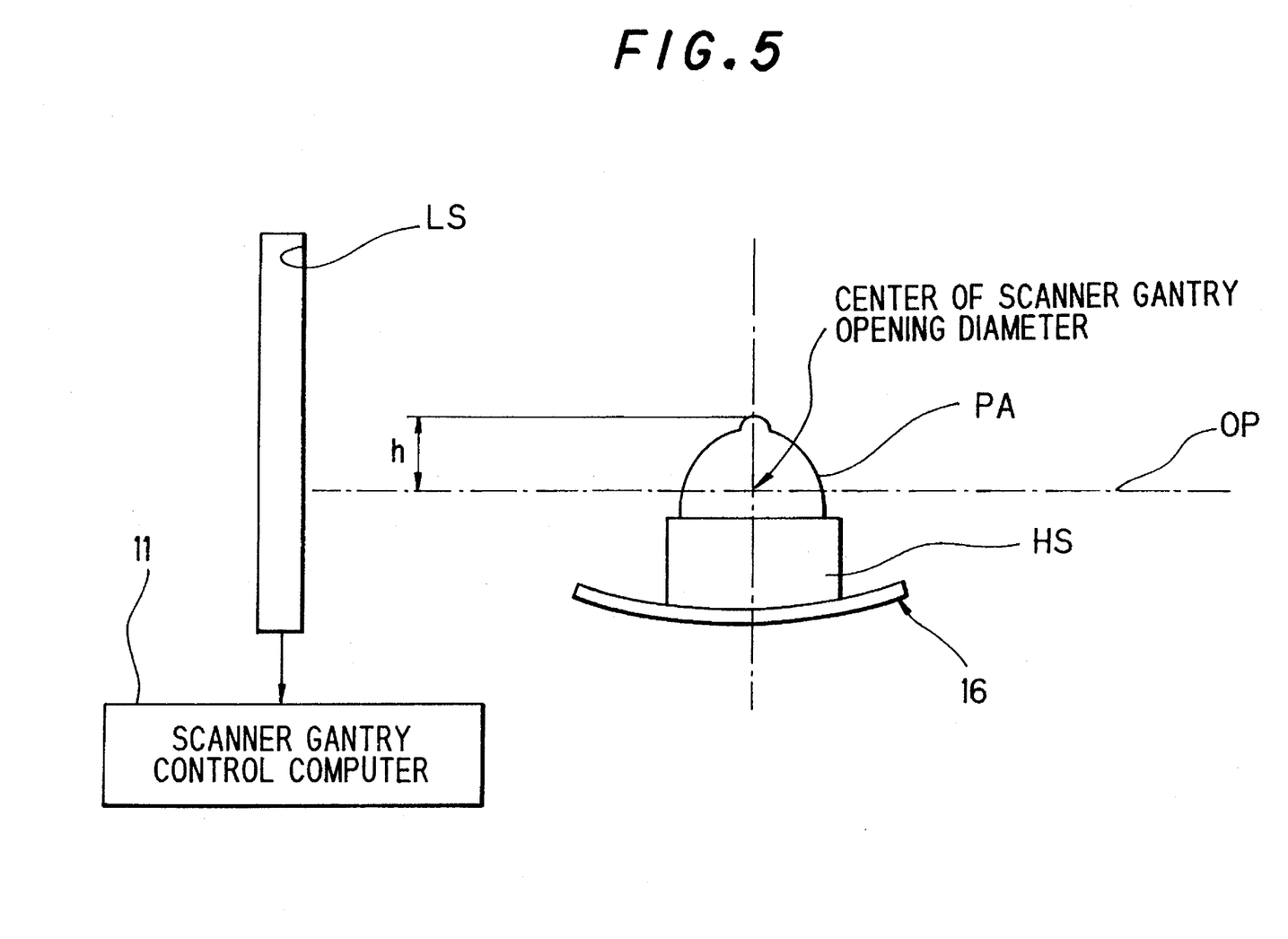
FIG. 5 shows a case in which the head of a patient is irradiated with X-rays in the X-ray CT apparatus of FIG. 1.

However, actually, as shown in FIGS. 4 and 5, since the patient PA placed on the top board 16 of the patient table 2 necessarily has a certain size, a height h shown in FIG. 4 should be subtracted from the height (or distance) H of Equations (1) and (2).

However, as shown in FIGS. 4 and 5, the surface of the patient PA is not a plane V12., is not flat. Considering this fact, it is sufficient for the operator to roughly recognize the image reconstruction computing area FOV and the X-ray irradiation area XRA shown in FIG. 3. Therefore, it is not necessary to strictly calculate the height (or distance) H shown in FIG. 3.

The height (or distance) H may be calculated with high accuracy In the following manner. A line sensor LS or the like is disposed at the side of the patient table 2 (see FIGS. 4 and 5), and the height h of the body surface of the patient PA is calculated based on an output of the line sensor LS. Considering the height h thus calculated, the scanner gantry control computer 11 calculates the height (or distance) H shown in FIG. 4. Thus, the swing angles θ1 and θ2 can be calculated easily.

FIGS. 4 and 5 show cases in which the abdomen and head of the patient PA placed on the top board 16 are irradiated with X-rays, respectively. The head is placed on a headrest HS.

Referring to FIG. 3, the depth B of the image reconstruction area FOV is determined by the swing angles θ of the swinging mirror 29 (42, 55), and the lateral width (in the direction perpendicular to the paper surface of FIG. 3) is determined by the opening degree of the drive-type slit mechanism 27 (40, 53) shown in FIG. 2.

Once the depth B is determined, the swing angles θ1 and θ2 are easily determined if the height (or distance) H is known. Values of the swing angles θ1 and θ2 are sent, as parameters for the Image reconstruction computing area FOV, via the central control computer 6.

Figure 6:
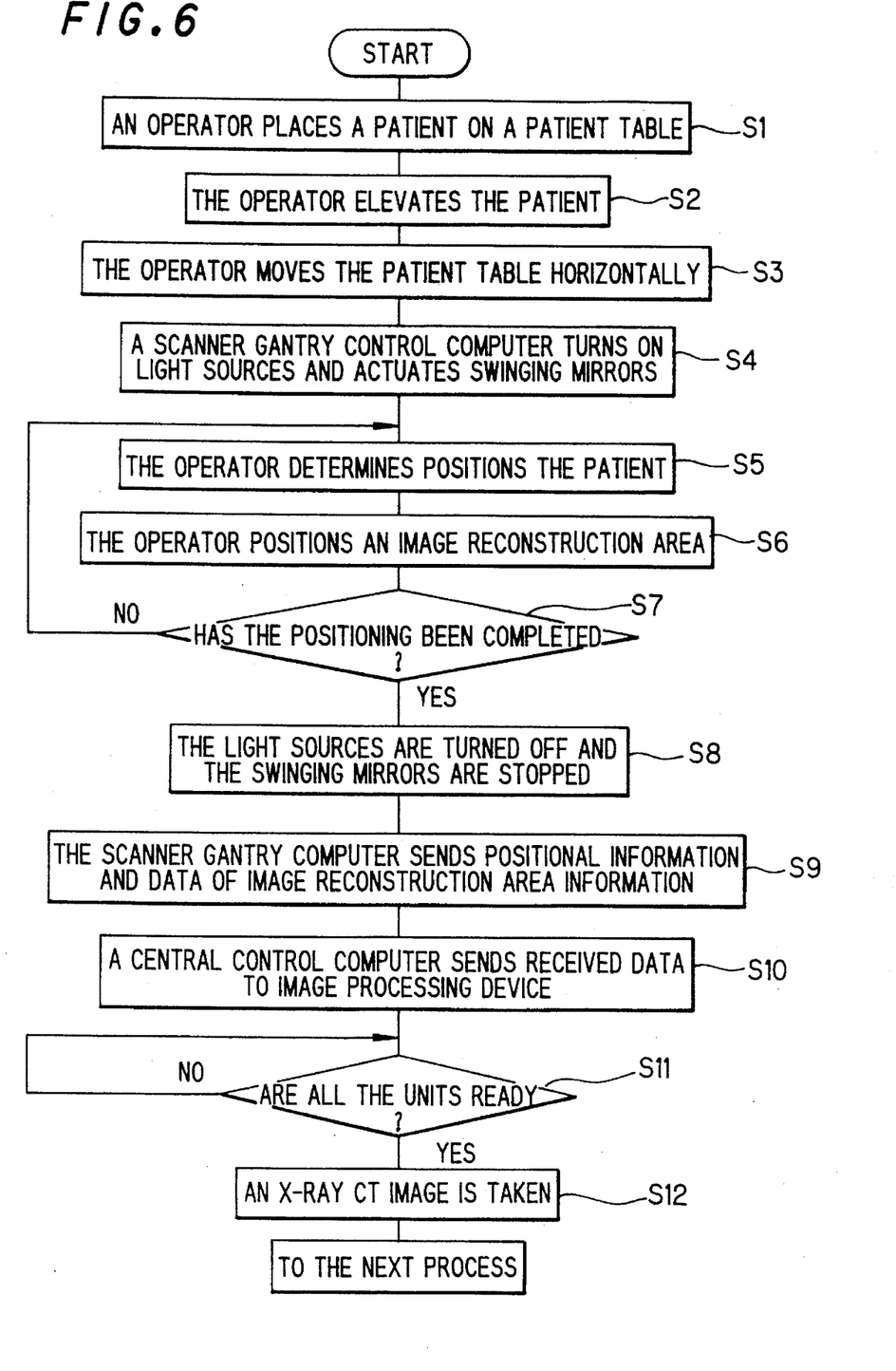
FIG. 6 is a flowchart showing an example of an operation of the X-ray CT apparatus of FIG. 1.

FIG. 6 shows an example of a procedure of taking an X-ray CT image according to the embodiment of the invention.

First, the operator places the patient PA on the patient table 2 (see FIG. 1; step S1). Then, the operator elevates the top board 16 of the patient table 2 (step S2), and horizontally moves the patient table 2 to place a part of the patient PA that is to be subjected to X-ray CT imaging in the opening 1a of the scanner gantry 1 (step S3).

Since the scanner gantry control computer 11 (see FIG. 1) can immediately detect that the operator moved the top board 16 of the patient table 2, it turns on the light sources (projectors) 25, 38 and 51. Then, the scanner gantry control computer 11 actuates the swinging mirrors 29, 42 and 55 to mark the surface of the patient PA with light (step S4).

Then, the operator positions the patient PA with respect to the scanner gantry 1 to take an X-ray image of the patient (step S5), and positions the image reconstruction area FOV (step S6).

After completion of the above positioning operations (steps S5–S7), the scanner gantry control computer turns off the light sources 25, 38 and 51, and stops the swinging mirrors 29, 42 and 55 (step S8).

Then, the scanner gantry control computer 11 communicates with the central control computer 6 to send it positional information of the top board 16 of the patient table 2, information on the image reconstruction area FOV, and other information (step S9).

Then, the central control computer 6 (see FIG. 2) sends the image processing device 5 the data as received from the scanner gantry control computer 11 (step S10). After confirming that all the units of the apparatus are ready (step S11), the central control computer 6 sends commands for X-ray Ct image taking to all the units to start the imaging (step S12).

As described above, according to the embodiment of the invention, the X-ray CT apparatus consists of the main body (scanner gantry) including the scanner for rotating the X-ray tube and the X-ray detector opposed to each other and the peripheral mechanism therefor, the patient table on which a patient is placed, the operation console, and the X-ray generating device. The patient is moved into the opening of the scanner gantry by means of the patient table.

The operator manipulates the patient table 2 so that the patient PA is located at the center of the opening 1a. In doing so, the operator uses the patient positioning projectors (localizers). To produce a marker of the X-ray irradiation area XRA and the image reconstruction area FOV on the patient PA, each localizer is constituted of a light source such as an incandescent lamp and optics consisting of a lens, slit, etc.

The X-ray CT apparatus of the embodiment has the following features:

(1) The swinging mirror is used in the optics of the localizer.

(2) The marker of light for the patient positioning is expanded from a line (conventional X-ray CT apparatus) to a surface.

(3) The operator is allowed to visually recognize the image reconstruction area by changing the swing angle of a swinging mirror such as a galvano mirror and the aperture of a slit.

(4) At the same time, the information on the image reconstruction area is automatically sent to the image processing device.

By controlling the swinging mirror, marking of light can be made for the X-ray irradiation area and the image reconstruction area, to thereby visually providing the operator with the quantitative information on the X-ray irradiation area and the image reconstruction area. This will improve the ease of manipulation and operation.

Further, the image reconstruction area can be set without requiring the operator to directly input it manually (improvements in the ease of manipulation and operation).

The invention can be applied to the conventional X-ray CT apparatuses and the three-dimensional X-ray CT apparatus (high expandability).

The three-dimensional X-ray CT apparatus uses a conical X-ray beam and has a large-capacity data processing device in which a transmission image obtained by the X-ray beam serves as 1-view data. In the ordinary X-ray CT apparatuses, a three-dimensional image is obtained by accumulation of two-dimensional data and image processing such as interpolation. On the other hand, the three-dimensional X-ray CT apparatus is intended to produce a three-dimensional image from the reconstruction computing stage.

Marking at regular intervals (pitches) can be made using light emitted from each localizer. By controlling the swinging mirror, marking of light can be made for the X-ray irradiation area and the image reconstruction area, to thereby visually providing the operator with the quantitative information on the X-ray irradiation area and the image reconstruction area. Therefore, the frequency of erroneously setting the image reconstruction area is reduced (improvements in the ease of manipulation and operation).

That is, using the optics including the swinging mirror and the drive-type slit, the X-ray irradiation area can be indicated as a surface. The information on the image reconstruction area can be sent to the image processing device while the operator is allowed to visually recognize the image reconstruction area.

It is noted that the invention is not limited to the above embodiment.

For example, the medical examination apparatus is not limited to the X-ray CT apparatus, but applicable to medical examination apparatuses of other kinds or in other fields that are equipped with the medical examination unit and the patient table, for instance, a MRI (magnetic resonance imaging) system and emission CT apparatuses (nuclear medical diagnostic systems) such as a nuclear magnetic resonance SPECT (single photon emission CT) apparatus and a PET (positron emission CT) apparatus.

As described above, according to the invention, in a medical examination such as imaging of an examination body by irradiation of X-rays, a marker of light allows an operator to easily recognize visually and quantitatively an information area for examination such as the X-ray irradiation area or reconstruction computing area.

What is claimed is:

1. A medical examination apparatus comprising:
    a medical examination unit for performing medical examination of an examination body; and
    medical examination area display means for indicating, with light, a medical examination area on the examination body placed in the medical examination unit;
    wherein the medical examination area display means comprises:
        a light source for emitting a beam of light; and
        an optical system for shaping the beam of light emitted from the light source into a beam which can be scanned in a single direction to produce a two-dimensional light illumination area on the examination body in accordance with the medical examination area;
    wherein the optical system comprises:
        light beam width setting means for selectively varying a width of the beam of light from said light source in a first direction to produce a beam of light having a length and a predetermined narrow width; and
        light scanning means for forming the two-dimensional light illumination area by scanning the examination body in a second direction with the beam of light having the predetermined narrow width;
    wherein the light beam width setting means is a slit which is selectively variable in width; and
    wherein the light scanning means is a swinging mirror which is located between said slit and the examination body, and which is driven to scan the beam of light which has passed through said slit over the examination body.

2. The medical examination apparatus according to claim 1, wherein the medical examination unit is used to irradiate the examination body with X-rays to obtain an X-ray image, and wherein the medical examination area is an X-ray irradiation area.

3. The medical examination apparatus according to claim 1, wherein the medical examination unit is used to irradiate the examination body with X-rays to obtain an X-ray image, and wherein the medical examination area is an image reconstruction area for the examination body in which area the X-ray image is to be obtained by irradiation of the X-rays.

4. A medical examination apparatus according to claim 1, further comprising sensor means which is responsive to the beam of light which is scanned in the second direction, for sensing a length variable.

5. A medical examination apparatus according to claim 4, further comprising computer means responsive at least to said sensor means, for receiving data from said sensor means and for processing the data in a manner which provides the image reconstruction area.

6. A medical examination apparatus comprising:
    a non-invasive examination unit for radiological examination of a patient; and
    illumination means for indicating, with visible light, an examination area on the patient, including:
        a light source for emitting a beam of light; and
        an optical system for shaping the beam of light emitted from the light source into a beam which can be scanned in a single direction to produce a two-dimensional light illumination area on the patient in accordance with the medical examination area comprising:
            a slit for selectively setting a width of the beam of light from the light source in a first direction; and
            a driven swinging mirror located between the slit and the examination area on the patient for scanning the beam of light which has passed through said slit in a second direction.

7. A medical examination apparatus according to claim 6, further comprising sensor means which is responsive to the beam of light which is scanned in the second direction, for sensing a length variable.

8. A medical examination apparatus according to claim 7, further comprising computer means responsive at least to said sensor means, for receiving data from said sensor means and for processing the data in a manner which provides the image reconstruction area.

9. A non-invasive radiological medical examination apparatus comprising:
- means for determining an image reconstruction area including:
- illumination means for illuminating an examination area on the patient, including:
  - a visible light source; and
  - an optical system for shaping the light emitted from the light source into a two-dimensional light illumination area on the patient including:
    - a slit for setting a width of the light in a first direction; and
    - a driven swinging mirror for scanning the light which has passed through said slit in a second direction;
- sensor means, responsive to the light which is scanned in the second direction, for sensing a length variable; and
- computer means responsive to at least said sensor means for receiving data from said sensor means and for processing the data in a manner which provides the image reconstruction area.

* * * * *